United States Patent [19]

Greene et al.

[11] Patent Number: 4,517,968
[45] Date of Patent: May 21, 1985

[54] COMPOSITE ORTHOSIS FOR ANKLE SPRAINS AND THE LIKE

[75] Inventors: Ted J. Greene, La Canada; George P. Irons, West Covina, both of Calif.

[73] Assignee: United States Manufacturing Company, Pasadena, Calif.

[21] Appl. No.: 484,484

[22] Filed: Apr. 13, 1983

[51] Int. Cl.³ .............................................. A61F 3/00
[52] U.S. Cl. .................................. 128/80 H; 128/166
[58] Field of Search ................ 128/80 R, 80 H, 80 F, 128/82, 88, 87 R, 166, 165

[56] References Cited

U.S. PATENT DOCUMENTS 4,320,748  3/1982  Racette et al. ..................... 128/80 F
4,378,793  4/1983  Mauldin et al. ................... 128/80 H

*Primary Examiner*—John D. Yasko
*Attorney, Agent, or Firm*—Christie, Parker & Hale

[57] ABSTRACT

A composite orthosis immobilizes an injured joint such as the ankle, wrist, elbow or knee joint. Generally, the orthosis has lateral and medial support members extending along opposite sides of a limb adjacent the injured joint, a brace secured to the limb on the opposite side of the injured joint, and pivot means hinging the lateral and medial support members to the brace. In one form of the invention, an ankle brace is provided by lateral and medial support members extending along lateral and medial sides of the lower leg above the ankle, a shell which fits around the foot, and a separate pivot for hinging each support member to the shell in the vicinity of the ankle axis of rotation. With the user's foot in the shell and the support members extending alongside the lateral and medial sides of the lower leg, a bandage is wrapped tightly around the support members above the ankle joint for tightly securing the lateral support members to the sides of the lower leg above the ankle joint. This immobilizes the ankle joint against lateral and medial movement and provides limited resistance against torsion while allowing forward and backward rotation about the ankle joint.

4 Claims, 2 Drawing Figures

COMPOSITE ORTHOSIS FOR ANKLE SPRAINS AND THE LIKE

FIELD OF THE INVENTION

This invention relates to orthotic braces; and more particularly, to a composite orthosis for immobilizing injured joints such as the ankle, elbow, wrist or knee joints.

BACKGROUND OF THE INVENTION

Ankle sprains are common injuries that often occur during sports activities. Sprained ankles are usually wrapped with an ace bandage for immobilizing the ankle at least partially while the sprain heals. It usually takes a few weeks for an ankle sprain to heal. More severe ankle sprains are usually taped or placed in a cast. Use of an ace bandage to immobilize an ankle sprain suffers a number of disadvantages. Wrapping with an ace bandage can be harmful with nonprofessional wrapping. Moreover, it is often necessary to unwrap and later re-wrap an ace bandage, and so professional wrapping is not easily available every time the ankle must be wrapped.

In many sports injuries, an ankle sprain requires more support than can be provided by an ace bandage. With severe sprains that are not placed in a cast, the trainer often tapes the ankle to provide additional support for protecting against stress placed on the ankle joint. In this way, a player can often continue playing or practicing on a sprained ankle. The trainer must be careful to protect against taping the ankle so tightly that circulation is cut off. Thus, taping the ankle should only be done by someone with professional training.

The present invention provides a composite orthosis that overcomes the disadvantages of using ace bandages or taping to immobilize an injured joint. The orthosis of this invention provides a reasonably stiff means of lateral support for the joint which provides better support than an ace bandage. In addition, the orthosis can be applied without the professional wrapping necessary for ace bandages. Thus, the protection provided is not inherent in the skillfulness of the wrapping. The orthosis is particularly useful for sports injuries, since it provides the additional lateral support for the injured joint. As a result, the orthosis can be used in place of taping. With sports injuries that must be placed in a cast, the player can come out of the cast early and use the orthosis of this invention when practicing or playing. The advantages of the present invention are provided for a number of injuries, such as sprains to the ankle, wrist, knee, or elbow, for example.

SUMMARY OF THE INVENTION

Briefly, the composite orthosis of this invention includes lateral and medial support members extending along lateral and medial sides of a first limb adjacent one side of a rotational joint such as the ankle joint. The support members are of sufficient stiffness to provide lateral and medial support along opposite sides of the first limb. A brace is secured to a second limb adjacent the opposite side of the joint. The brace provides lateral and medial support for the second limb. A pivot attaches the lateral and medial support members to the brace so the lateral and medial support members can pivot about an axis through the joint. A bandage is wrapped tightly around the first limb and the lateral and medial support members. The resulting combination provides resistance against sideways motion of each limb, as well as a useful amount of resistance against twisting of one limb relative to the other. The limb supported by the lateral and medial support members and the bandage is able to pivot normally forward and backward about the axis of the joint.

One form of the invention provides a composite orthosis for ankle sprains in which the lateral and medial support members extend along opposite sides of the lower leg above the ankle joint, and in which the lower ends of the support members are hinged to opposite sides of a brace in the form of a shell for extending around the foot. The bandage is wrapped around the support members, and the combination provides good resistance against lateral or medial movement of the lower leg relative to the ankle joint. However, lower leg is able to rotate forward or backward about the ankle joint, so that normal rotation of the ankle joint in one plane of movement is not interfered with by use of the orthosis. The orthosis also can include padding for the insides of the lateral and medial support members and a non-slip surface on the outside of the support members to ensure a tight wrapping of the bandage around the support members.

These and other aspects of the invention will be more fully understood by referring to the following detailed description and the accompanying drawings.

DRAWINGS

DETAILED DESCRIPTION

Figure 1:
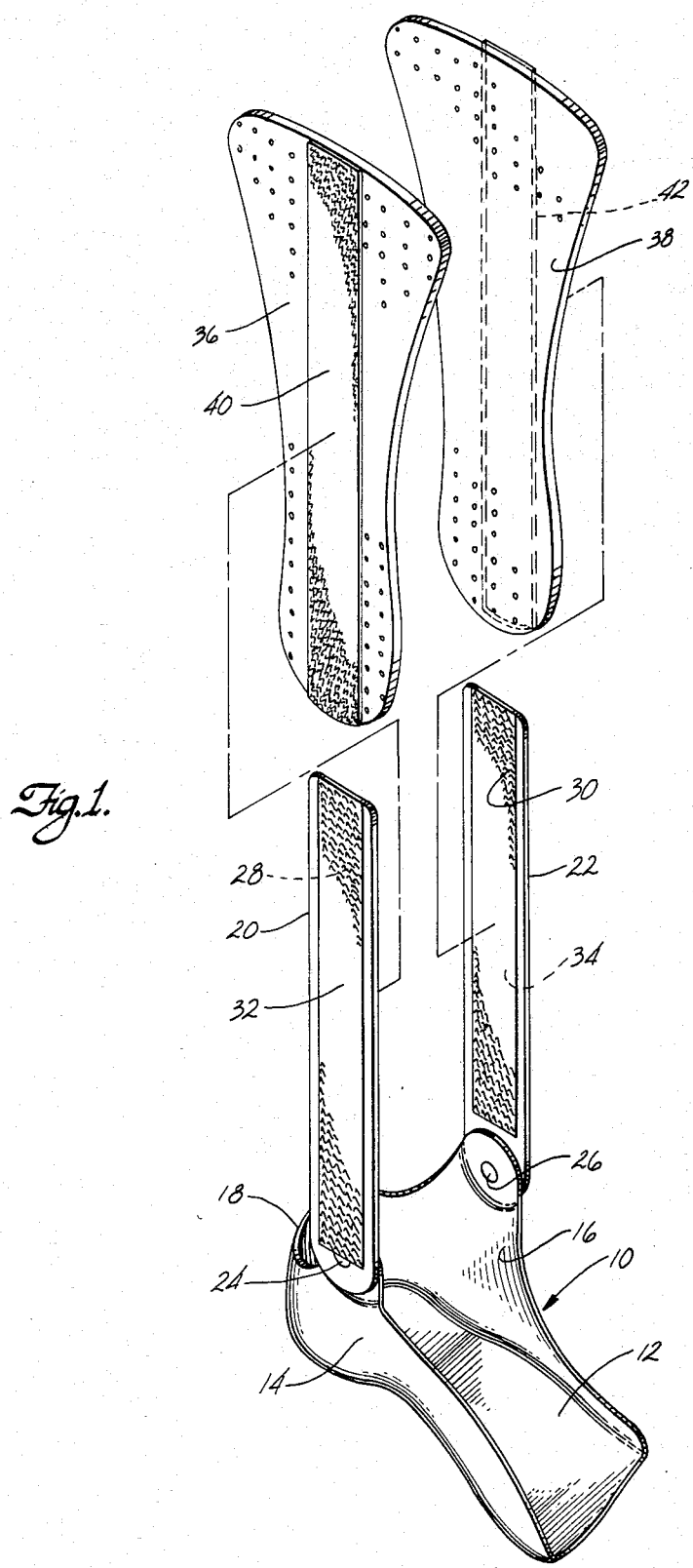
FIG. 1 is an exploded perspective view illustrating components of a composite orthosis according to the principles of this invention.

FIG. 1 shows components of a composite orthosis for bracing the ankle, which is one embodiment of the invention. It includes a brace or shell 10 for supporting the user's foot. The shell includes a foot plate 12 for supporting the bottom of the foot, vertical lateral and medial side walls 14 and 16 for extending around the lateral and medial sides of the foot, and a rounded posterior wall 18 for fitting around the heel. The shell is preferably made of a hard relatively stiff plastic material such as polyethelene. The shell conforms closely to the shape of the foot and can be worn inside the user's shoe, if desired.

Narrow, elongated lateral and medial uprights 20 and 22 extend vertically above the lateral and medial side walls of the shell. The lateral and medial uprights are attached to the shell through lateral and medial pivots 24 and 26, respectively. The pivots are aligned on a common axis through the axis of rotation of the ankle joint. The lateral and medial uprights are made of a semi-rigid plastic material so that each is capable of yielding slightly in torsion while also being somewhat bendable inwardly or outwardly toward or away from the upright on the opposite side. Each upright can pivot independently of the other about its corresponding pivot.

Fastening means are attached to the insides of the lateral and medial uprights. These preferably include elongated strips of thistle cloth fasteners sold under the trademark Velcro; and in the illustrated embodiment, fasteners 28 and 30 of the hook type Velcro material are attached to the insides of the lateral and medial uprights, respectively.

An anti-slip material is affixed to the outer faces of the lateral and medial uprights. Preferably, such anti-slip surfaces are provided by elongated sections of Velcro hook-type fasteners 32 and 34 secured to the outer faces of the lateral and medial uprights. The hook-type fasteners on the inside and outside faces of each upright are preferably secured to the uprights by adhesive bonding with conventional adhesives known in the art.

Lateral and medial resilient foam pads 36 and 38 are adapted for attachment to the inside faces of the lateral and medial uprights, respectively. Elongated lateral and medial strips 40 and 42 of Velcro type pile material are affixed to outside faces of the foam pads. The fasteners 40 and 42 on the foam pads are adapted for attachment to the Velcro type hook fasteners 32 and 34 on the inside faces of the uprights. The foam pads are adapted to overlie the lateral and medial sides of the user's ankle and opposite sides of the lower leg above the ankle during use of the composite orthosis.

Figure 2:
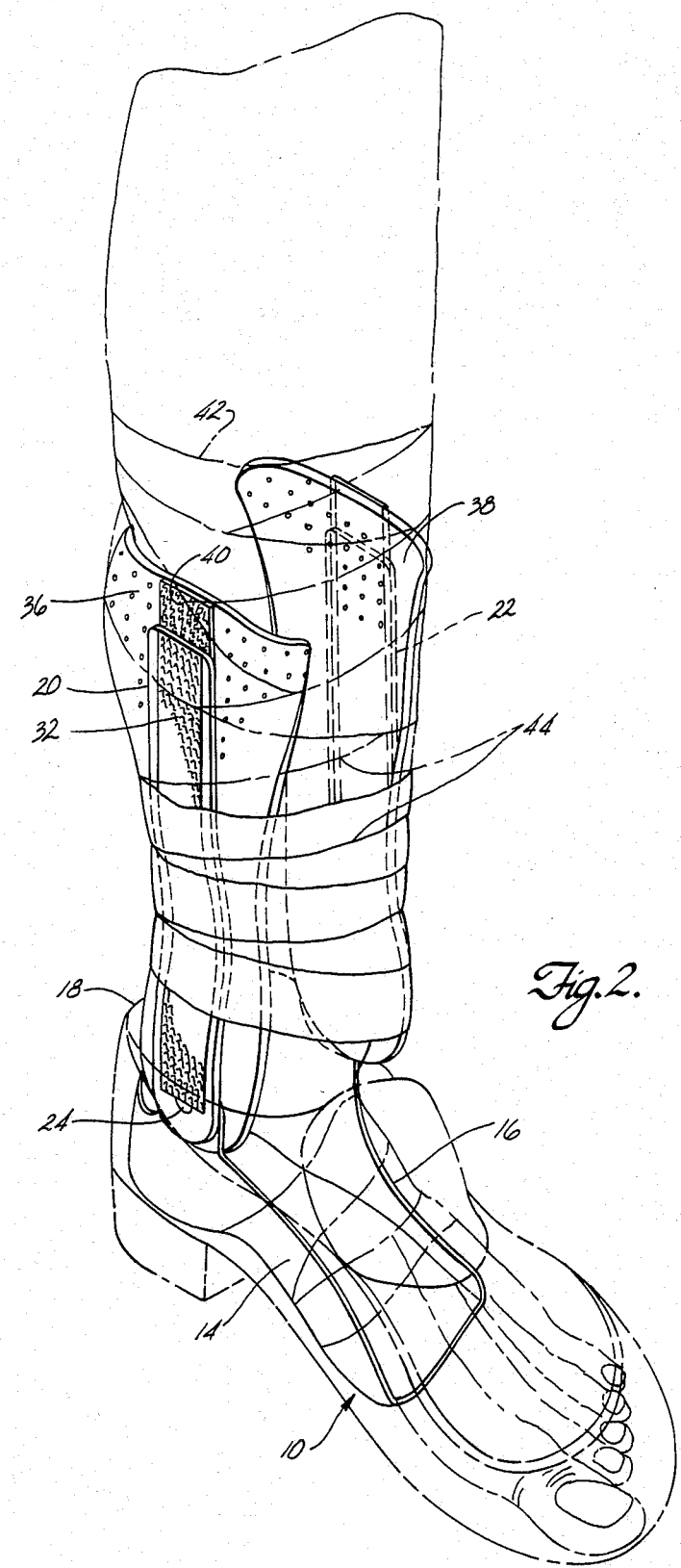
FIG. 2 is a perspective view illustrating use of the orthosis.

In using the composite orthosis, the user's ankle region and lower leg is first wrapped with a flexible bandage (not shown) from the ankle bone up to just below the knee. A preferred bandage for this purpose is a self-adherent wrap sold under the trademark Coban by the Medical Products Division of 3M Company. The bandage need not be professionally wrapped but is simply applied to provide an additional amount of resistance against twisting of the lower leg and slippage between the lower leg and the uprights. The lateral and medial foam pads are then affixed to inside faces of the uprights, as illustrated in FIG. 2, by attaching the cooperating Velcro fasteners on the pads and the uprights. The user's foot is then placed in the shell so that the size of the shell surrounds the sides and rear of the foot. The side walls of the shell are yieldable inwardly to conform to the shape of the foot below and in the vicinity of the ankle joint. The uprights 20 and 22 extend along the lateral and medial sides of the lower leg above the ankle joint. The uprights are yieldable laterally along their length so they can conform to the shape of the lateral and medial sides of the lower leg above the ankle. With the foot in place in the shell and the uprights overlying opposite sides of the lower leg, open spaces are provided along the front and rear of the lower leg between the uprights. A self-adhesive elastic bandage 44 is then wrapped tightly around the outside faces of the uprights from the vicinity of the ankle joint upwardly above the upper ends of the uprights. Thus, the only means of support along the front and rear of the lower leg are provided by the wrapping. The bandage can be the self-adherent wrap sold by 3M Company under the Coban trademark. The bandage can be applied with non-professional wrapping simply as a series of loops wound in overlapping fashion and pulled tightly so that the lateral and medial sides of the foot below the ankle joint, at the ankle joint, and above the ankle joint are firmly supported by the rigidity of the shell and the uprights. The anti-slip surfaces on the uprights keep the wrapping in place and assist in the usefulness of the brace without professional wrapping. The wrapping combined with the stiffness of the brace also provides an amount of resistance to twisting of the foot or the lower leg about the ankle joint. The wrapping is sufficiently flexible to allow the user to have nearly normal ankle mobility for forward and rear movement about the axis through the ankle joint. The pivots attaching the uprights to the shell permit normal rotation of the ankle joint.

The composite orthosis provides greater lateral and medial immobilization of the ankle joint than a professionally wrapped ace bandage. However, the orthosis allows some rotation (twisting) of the ankle joint which can be desirable. The orthosis allows a normal amount of forward and rear motion about the ankle joint. Thus, the user has a useful combination of immobilization laterally and medially, limited twisting motion against a useful level of resistance, and nearly normal forward and rear rotation about the joint. This combination is provided without requiring professional wrapping. The composite orthosis is particularly useful on more severe sprains that ordinarily may require taping by a professional trainer or the like. The orthosis allows sufficient freedom of movement of the ankle joint such that a player whose ankle has been in a cast can come out of the cast and begin playing or practicing earlier than when the ankle is taped or an ace bandage is used.

The composite orthosis of this invention also can be used for immobilizing injuries to other joints such as the elbow, knee or wrist joints. In these instances, a brace is affixed to a limb on one side of the joint. Support members similar to the uprights used in the ankle brace are hinged to the support. The support members pivot about an axis through the joint, and the support members extend along the sides of the limb to provide stiffness necessary for lateral and medial resistance. An elastic bandage is then tightly wrapped around the support members to provide good resistance laterally and medially, while allowing a certain freedom of rotation about the axis of the joint. For a knee orthosis, it is desirable to wrap the bandage around portions of the brace extending along lateral and medial sides of the lower and upper leg, while leaving the knee joint itself open.

What is claimed is:

1. A composite orthosis for use in immobilizing a rotational joint comprising:
    elongated semi-rigid lateral and medial support members extending along lateral and medial sides of a first limb adjacent a rotational joint;
    a brace secured to a second limb on an opposite side of the joint;
    means hinging the lateral and medial support members to the brace so the support members can pivot relative to the brace about an axis through the joint, front and rear open regions being left along the front and rear of the first limb between the support members;
    resilient lateral and medial padding and means for attaching the padding to the inside faces of the lateral and medial support members so the resilient padding overlies the lateral and medial sides of the first limb;
    non-skid surfaces on the outer faces of the lateral and medial support members; and
    a self-adherent elastic bandage wrapped around the lateral and medial support members and the front and rear open regions of the first limb between the support members, the elastic bandage being wrapped in a series of overlapping loops from the vicinity of the joint along the length of the first limb and into frictional contact with the non-skid surfaces on the outer faces of the lateral and medial support members to prevent slippage of the bandage wrapped around the support members and to firmly support the lateral and medial support members against the lateral and medial sides of the first limb, while the wrapping of the elastic bandage provides the means of support along the front and rear of the first limb between the lateral and medial support members, the lateral and medial support members and the brace cooperating for immobilizing the joint against lateral and medial mobility, the pivot means and the wrapping of the elastic bandage along the front and rear of the first limb allowing rotational mobility of the limb about the joint axis, while providing resistance to twisting of one limb relative to the other.

2. Apparatus according to claim 1 including means for releasably attaching the resilient padding to the inside faces of the lateral and medial support members.

3. A composite orthosis for immobilizing the ankle joint comprising:

- elongated semi-rigid lateral and medial support members extending along the lateral and medial sides of the lower leg above the ankle;
- a foot support for making a snug fit around the foot, the foot support having lateral and medial side portions overlying the lateral and medial sides of the ankle joint;
- pivot means rotatably attaching the lateral and medial support members to the lateral and medial side portions of the foot support so the lateral and medial support members can pivot about an axis substantially though the ankle joint when the foot is placed in the foot support, the support members having an open region between them above the foot support;
- resilient lateral and medial pads extending along the lateral and medial sides of the ankle joint and means for attaching the pads to the inside faces of the lateral and medial support members so the lateral and medial pads overlie the lateral and medial sides of the ankle joint;
- non-skid surfaces on the outer faces of the lateral and medial support members; and
- a self-adherent elastic bandage wrapped tightly around the lateral and medial support members and the front and rear open regions between the support members, the elastic bandage being wrapped in a series of overlapping loops from the vicinity of the ankle joint along the lower leg and into frictional contact with the non-skid outer surfaces on the lateral and medial support members to prevent slippage of the bandage wrapped around the support members and to firmly support the lateral and medial support members against the lateral and medial sides of the lower leg, while the wrapping of the elastic bandage provides the means of support along the front and rear of the lower leg between the lateral and medial support members, the support members and the foot support cooperating to immobilize the ankle in lateral and medial directions, the pivot means and the wrapping of the elastic bandage along the front and rear of the lower leg allowing rotation of the lateral and medial support members about the ankle joint, while providing resistance to twisting of the lower leg relative to the ankle joint.

4. Apparatus according to claim 3 including means for releasably attaching the padding to the inside faces of the support members.

* * * * *